United States Patent
Durham

(10) Patent No.: US 11,684,107 B2
(45) Date of Patent: Jun. 27, 2023

(54) SOUND AMPLIFYING BOWL ASSEMBLY

(71) Applicant: Christopher J. Durham, San Clemente, CA (US)

(72) Inventor: Christopher J. Durham, San Clemente, CA (US)

(*) Notice: Subject to any disclaimer, the term of this patent is extended or adjusted under 35 U.S.C. 154(b) by 346 days.

(21) Appl. No.: 16/844,211

(22) Filed: Apr. 9, 2020

(65) Prior Publication Data

US 2021/0315311 A1 Oct. 14, 2021

(51) Int. Cl.
*A42B 3/30* (2006.01)
*A61F 11/30* (2022.01)

(52) U.S. Cl.
CPC .............. *A42B 3/30* (2013.01); *A61F 11/30* (2022.01)

(58) Field of Classification Search
CPC .............. A42B 3/30; A42B 3/16; A61F 11/30
See application file for complete search history.

(56) References Cited

U.S. PATENT DOCUMENTS

| | | | | |
|---|---|---|---|---|
| 12,951 | A * | 5/1855 | Hyde | A61F 11/30 181/136 |
| 1,761,666 | A | 6/1930 | Hinternesch | |
| 2,643,729 | A * | 6/1953 | McCracken | H04R 5/027 181/158 |
| 2,810,445 | A | 10/1957 | Garrido | |
| 3,021,526 | A | 2/1962 | Lastnik | |
| 3,513,937 | A * | 5/1970 | Moshier | G09B 23/30 181/129 |
| 3,602,329 | A | 8/1971 | Mattis | |
| 3,938,616 | A | 2/1976 | Brownfield | |
| 4,979,586 | A * | 12/1990 | Lazzeroni | A42B 3/166 381/372 |
| 4,997,056 | A * | 3/1991 | Riley | A61F 11/30 181/129 |
| 5,189,265 | A * | 2/1993 | Tilkens | A42B 1/004 181/136 |
| 5,361,419 | A | 11/1994 | Bernstein | |
| 5,632,048 | A | 5/1997 | Mortell | |
| 5,691,515 | A | 11/1997 | Landis | |
| 5,696,356 | A | 12/1997 | Dudley | |
| 6,073,272 | A * | 6/2000 | Ball | A42B 3/16 2/423 |
| 6,082,486 | A * | 7/2000 | Lee | A61F 11/30 181/136 |

(Continued)

FOREIGN PATENT DOCUMENTS

WO WO2018229619 12/2018

*Primary Examiner* — Edgardo San Martin

(57) ABSTRACT

A sound amplifying bowl assembly includes a grommet has an inner lip that is spaced from an outer lip to define an engaging slot between the inner lip and the outer lip. The inner lip is extendable through an ear hole in a helmet thereby facilitating a bounding edge of the ear hole to engage the engaging slot. In this way the grommet is retained in the ear hole. The grommet has a sound hole extending therethrough to pass audible sound into the helmet. A bowl is integrated into the grommet and the bowl is concavely arcuate such that a curvature of the bowl has a focus that is aligned with the sound hole in the grommet. In this way the bowl can direct the audible sound into the ear hole. Thus, the bowl enhances a user's ability to hear the audible sound when the user is wearing the helmet.

7 Claims, 4 Drawing Sheets

(56) References Cited

U.S. PATENT DOCUMENTS

| | | | | |
|---|---|---|---|---|
| 6,708,339 B1* | 3/2004 | Smith, Jr. | ............... | A42B 3/20 |
| | | | | 2/9 |
| 6,874,169 B2* | 4/2005 | Broersma | ............... | A42B 3/30 |
| | | | | 2/209 |
| 7,430,300 B2 | 9/2008 | Vosburgh | | |
| 8,474,064 B2* | 7/2013 | Hardy, III | ............... | A42B 3/16 |
| | | | | 2/244 |
| 8,973,172 B2* | 3/2015 | Daniel | ................ | A42B 3/166 |
| | | | | 2/410 |
| 2020/0178638 A1* | 6/2020 | Morales Velasquez | . | A42B 3/16 |

* cited by examiner

SOUND AMPLIFYING BOWL ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to amplifying devices and more particularly pertains to a new amplifying device for passively amplifying sound passing through an ear hole in a helmet.

(2) Description of Related Art Including Information Disclosed Under 37 CFR 1.97 and 1.98

The prior art relates to amplifying devices. The prior art discloses a horn that has a spiral sound tube which is worn on a user's head for passively amplifying sounds for the user's ear. The prior art discloses a horn that includes a cushion that is positioned in a user's ear to passively amplify ambient sounds. Additionally, the prior art discloses an ear muff that has a passive speaker therein, that can be worn beneath a helmet, for passively amplifying ambient sound passing through an ear hole in the helmet. The prior art discloses an active noise cancelling device that is mounted on a user's ear when the user wears a helmet. The prior art also discloses a bowl that is wearable around a user's ear to passively amplify ambient sounds for the user.

BRIEF SUMMARY OF THE INVENTION

An embodiment of the disclosure meets the needs presented above by generally comprising a grommet has an inner lip that is spaced from an outer lip to define an engaging slot between the inner lip and the outer lip. The inner lip is extendable through an ear hole in a helmet thereby facilitating a bounding edge of the ear hole to engage the engaging slot. In this way the grommet is retained in the ear hole. The grommet has a sound hole extending therethrough to pass audible sound into the helmet. A bowl is integrated into the grommet and the bowl is concavely arcuate such that a curvature of the bowl has a focus that is aligned with the sound hole in the grommet. In this way the bowl can direct the audible sound into the ear hole. Thus, the bowl enhances a user's ability to hear the audible sound when the user is wearing the helmet.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
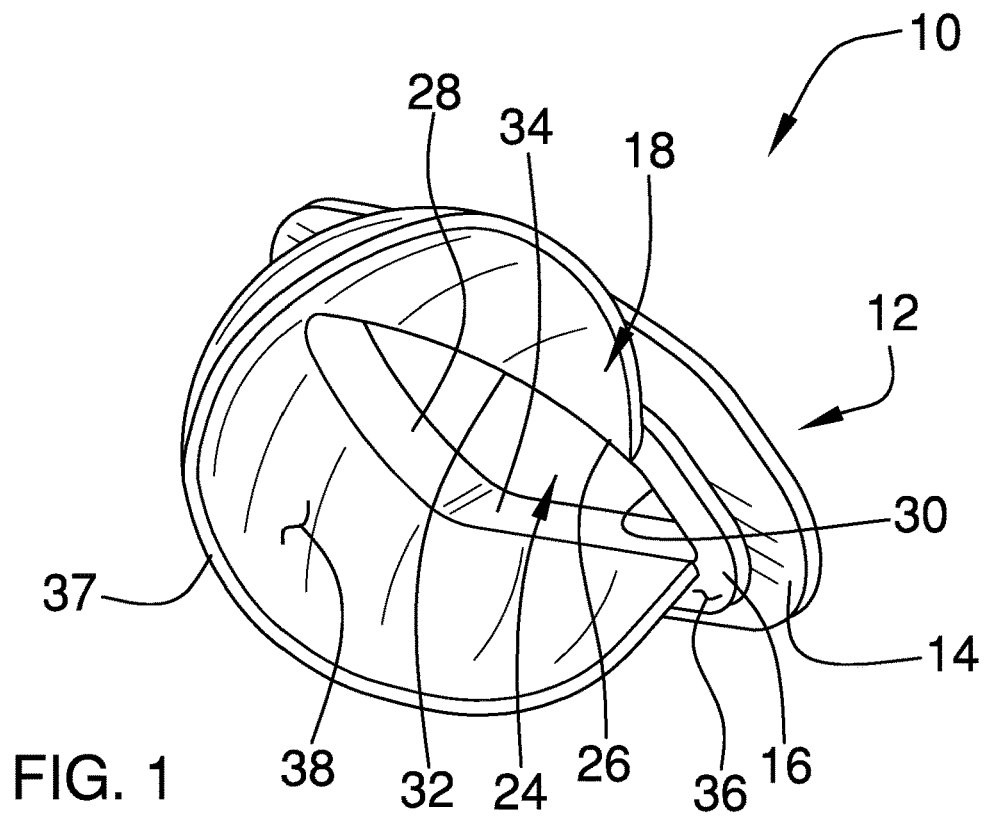
FIG. 1 is a front perspective view of a sound amplifying bowl assembly according to an embodiment of the disclosure.
Figure 2:
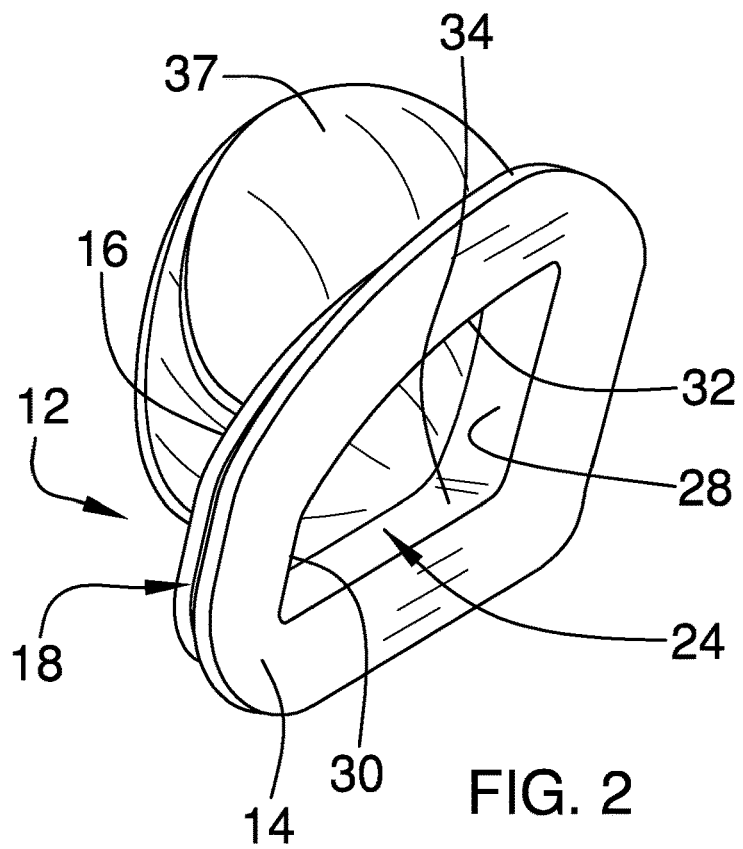
FIG. 2 is a back perspective of an embodiment of the disclosure.
Figure 3:
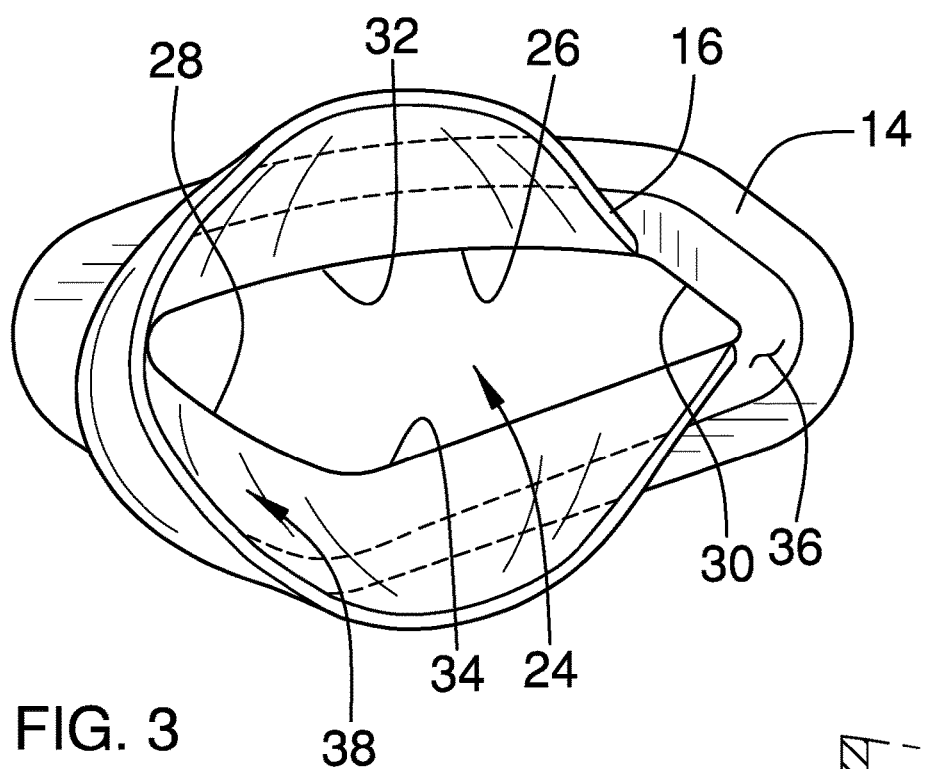
FIG. 3 is a front phantom view of an embodiment of the disclosure.
Figure 4:
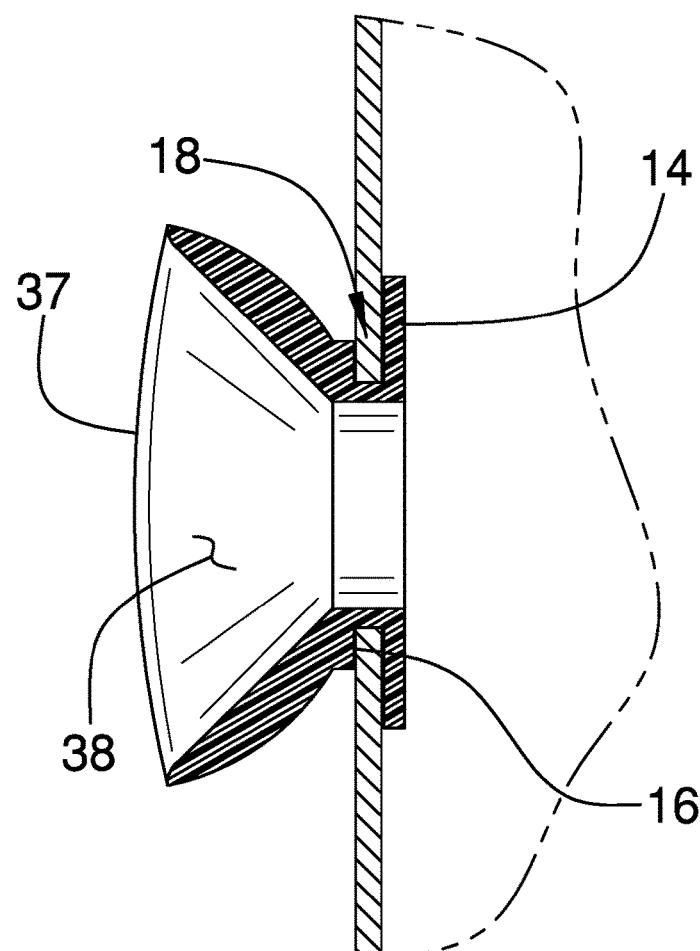
FIG. 4 is a cross sectional view taken along line 4-4 of FIG. 5 of an embodiment of the disclosure.
Figure 5:
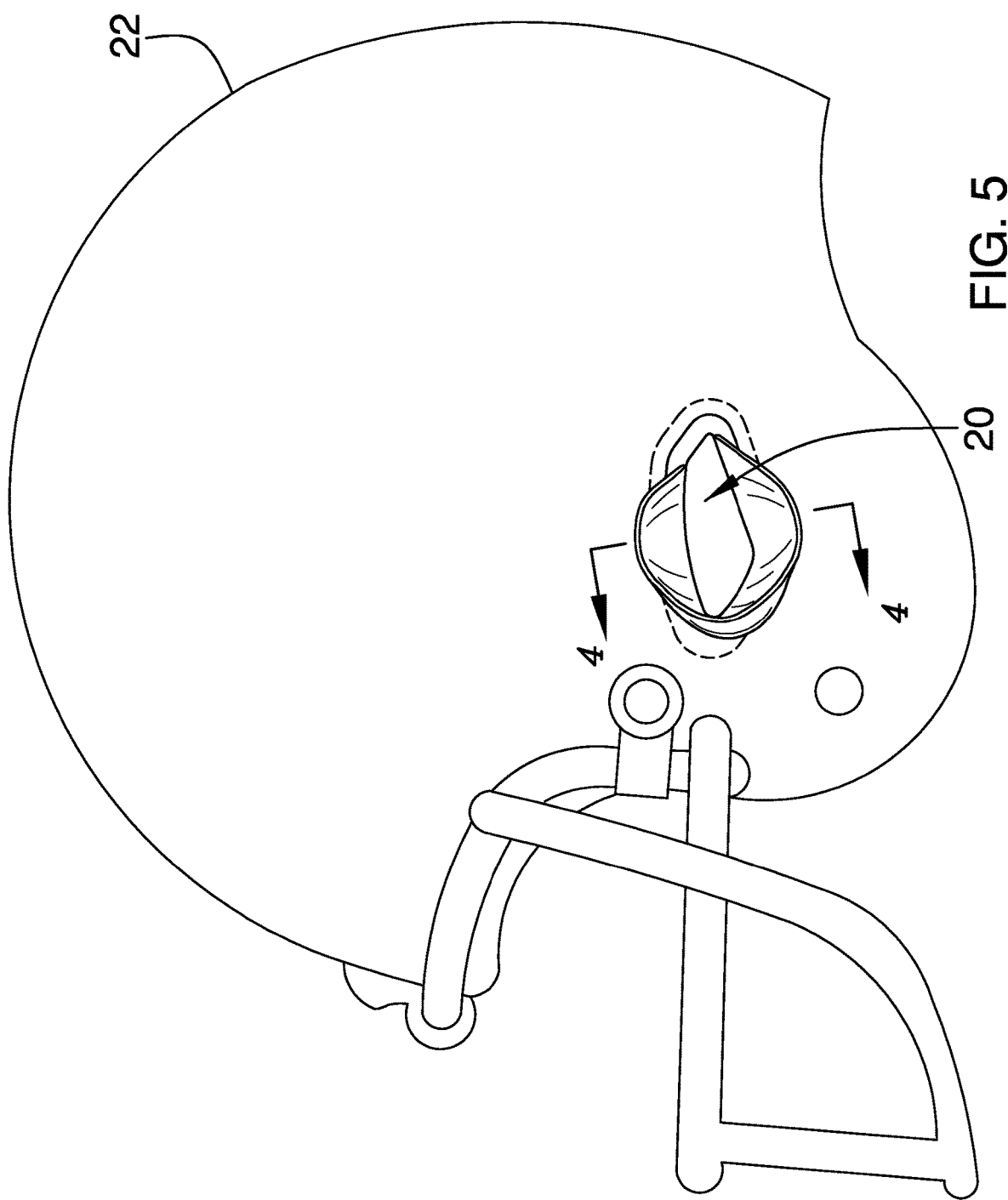
FIG. 5 is a front view of an embodiment of the disclosure in use.
Figure 6:
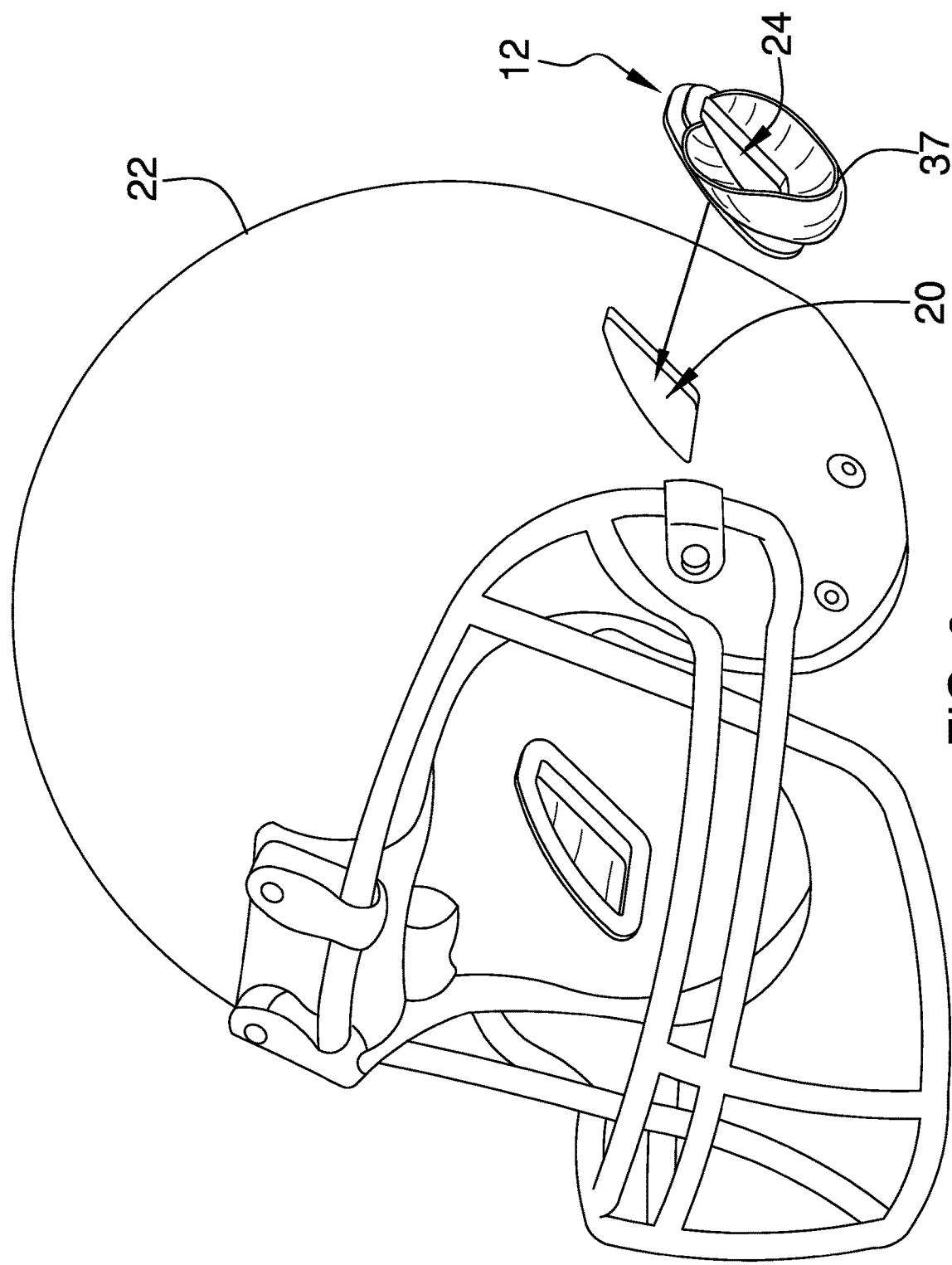
FIG. 6 is an exploded perspective in-use view of an embodiment of the disclosure.

With reference now to the drawings, and in particular to FIGS. 1 through 6 thereof, a new amplifying device embodying the principles and concepts of an embodiment of the disclosure and generally designated by the reference numeral 10 will be described.

As best illustrated in FIGS. 1 through 6, the sound amplifying bowl assembly 10 generally comprises a grommet 12 that has an inner lip 14 that is spaced from an outer lip 16 to define an engaging slot 18 between the inner lip 14 and the outer lip 16. The inner lip 14 is extendable through an ear hole 20 in a helmet 22 thereby facilitating a bounding edge 23 of the ear hole 20 to engage the engaging slot 18. In this way the grommet 12 is retained in the ear hole 20. The helmet 22 may be an American football helmet, a base ball helmet or any other helmet that not only covers a user's ears but also has an ear hole. Additionally, the inner lip 14 has a perimeter that is greater than the perimeter of the outer lip 16.

The grommet 12 has a sound hole 24 extending therethrough to pass audible sound into the helmet 22. The sound hole 24 has a bounding edge 26 and the bounding edge 26 has a front side 28, a back side 30, a top side 32 and a bottom side 34. The top side 32 slopes downwardly between the front side 28 and the back side 30 thereby facilitating the sound hole 24 to conform to the shape of the ear hole 20 in the helmet 22. As is most clearly shown in FIG. 3, the bounding edge 26 of the sound hole 24 may have a diamond shape for conforming to the shape of the ear hole 20 in a helmet 22 that is approved for use in the National Football League. Moreover, the outer lip 16 has an outwardly facing surface 36 that is exposed when the grommet 12 is positioned in the ear hole 20. The grommet 12 may be comprised of silicone, or other similar type of resiliently deformable material, thereby facilitating the grommet 12 to be fitted into the ear hole 20.

A bowl 37 provided and the bowl 37 is integrated into the grommet 12. Moreover, the bowl 37 is concavely arcuate such that the curvature of the bowl 37 has a focus that is aligned with the sound hole 24 in the grommet 12. In this way the bowl 37 can direct the audible sound into the ear hole 20 for enhancing the user's ability to hear the audible sound when the user is wearing the helmet 22. The bowl 37 extends away from the outwardly facing surface 36 of the outer lip 16 and the bowl 37 extends along each of the front side 28, the top side 32 and the bottom side 34 of the bounding edge 26 of the sound hole 24. In this way the bowl 37 simulates the shape of a human outer ear. The bowl 37 has a reflecting surface 38 that is directed toward the sound hole 24 and the reflecting surface 38 is concavely arcuate. The bowl 37 shields the front side 28, the top side 32 and the bottom side 34 of the bounding edge 26 from ambient noise, while the bowl 37 facilitates audible sounds to pass over the top side 32 of the bounding edge 26. In this way the bowl 37 enhances the user's ability to hear the voices of players on their team while simultaneously reducing the intensity of crowd noise and other ambient sounds.

In use, the grommet 12 is inserted into the ear hole 20 in the helmet 22 having the bowl 37 being exposed on the helmet 22. In this way the bowl 37 reflects and passively amplifies audible sounds into the ear hole 20. Thus, the user can more clearly hear the audible sounds such as plays called during a football game or other sounds that might be otherwise difficult to hear. Additionally, the orientation of the bowl 37 on the grommet 12 reduces the intensity of crowd noise and other ambient sounds for the user.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A sound amplifying bowl assembly being insertable into an ear hole in a helmet for amplifying sound passing through the ear hole, said assembly comprising:
    a grommet having an inner lip being spaced from an outer lip to define an engaging slot between said inner lip and said outer lip, said inner lip being extendable through an ear hole in a helmet thereby facilitating a bounding edge of the ear hole to engage said engaging slot wherein said grommet is configured to be retained in the ear hole, said grommet having a sound hole extending therethrough wherein said sound hole is configured to pass audible sound into the helmet, said sound hole having a bounding edge, said bounding edge having a front side, a back side, a top side and a bottom side, said top side sloping downwardly between said front side and said back side thereby facilitating said sound hole to conform to the shape of said ear hole in said helmet, said outer lip having an outwardly facing surface being exposed when said grommet is positioned in said ear hole; and
    a bowl integrated into said grommet, said bowl being concavely arcuate such that a curvature of said bowl has a focus being aligned with said sound hole in said grommet thereby facilitating said bowl to direct the audible sound into said ear hole wherein said bowl is configured to enhance a user's ability to hear the audible sound when the user is wearing the helmet, said bowl extending away from said outwardly facing surface of said outer lip, said bowl extending along each of said front side, said top side and said bottom side of said bounding edge of said sound hole wherein said bowl is open facing said back side of said bounding edge wherein said bowl is configured to simulate the shape of a human outer ear facing rearwardly on the helmet, said bowl having a reflecting surface being directed toward said sound hole, said reflecting surface being concavely arcuate.

2. The assembly according to claim 1, wherein said sound hole has a bounding edge, said bounding edge having a front side, a back side, a top side and a bottom side, said top side sloping downwardly between said front side and said back side wherein said sound hole is configured to conform to the shape of the ear hole in the helmet.

3. The assembly according to claim 1, wherein said outer lip has an outwardly facing surface being exposed when said grommet is positioned in the ear hole.

4. The assembly according to claim 3, wherein:
    said sound hole has a bounding edge, said bounding edge having a front side, a back side, a top side and a bottom side, said top side sloping downwardly between said front side and said back side wherein said sound hole is configured to conform to the shape of the ear hole in the helmet; and
    said bowl extends away from said outwardly facing surface of said outer lip, said bowl extending along each of said front side, said top side and said bottom side said bounding edge of said sound hole.

5. The assembly according to claim 4, wherein said bowl has a reflecting surface being directed toward said sound hole, said reflecting surface being concavely arcuate.

6. A sound amplifying bowl system for amplifying sound passing through an ear hole in a helmet, said assembly comprising:

a helmet having an ear hole extending therethrough wherein said ear hole is configured to pass audible sounds therethrough, said ear hole having a bounding edge;

a grommet having an inner lip being spaced from an outer lip to define an engaging slot between said inner lip and said outer lip, said inner lip being extendable through an ear hole in a helmet thereby facilitating said bounding edge of said ear hole to engage said engaging slot for retaining said grommet in said ear hole, said grommet having a sound hole extending therethrough wherein said sound hole is configured to pass audible sound into said helmet, said sound hole having a bounding edge, said bounding edge having a front side, a back side, a top side and a bottom side, said top side sloping downwardly between said front side and said back side thereby facilitating said sound hole to conform to the shape of said ear hole in said helmet, said outer lip having an outwardly facing surface being exposed when said grommet is positioned in said ear hole; and a bowl integrated into said grommet, said bowl being concavely arcuate such that the curvature of said bowl has a focus being aligned with said sound hole in said grommet thereby facilitating said bowl to direct the audible sound into said ear hole wherein said bowl is configured to enhance a user's ability to hear the audible sound when the user is wearing the helmet, said bowl extending away from said outwardly facing surface of said outer lip, said bowl extending along each of said front side, said top side and said bottom side of said bounding edge of said sound hole wherein said bowl is open facing said back side of said bounding edge wherein said bowl is configured to simulate the shape of a human outer ear facing rearwardly on the helmet, said bowl having a reflecting surface being directed toward said sound hole, said reflecting surface being concavely arcuate.

7. A method of passively amplifying sound passing through an ear hole of a helmet, the steps of the method comprising:

providing a grommet having a sound hole extending therethrough;

providing a bowl being integrated into said grommet, said bowl being aligned with said sound hole, said bowl being concavely arcuate with respect to said sound hole wherein said bowl is configured to direct audible sound into said sound hole, said bowl extending along each of a front side, a top side and a bottom side of a bounding edge of said sound hole wherein said bowl is open facing said back side of said bounding edge wherein said bowl is configured to simulate a shape of a human outer ear; and inserting said grommet into an ear hole in a helmet such that said back side faces rearwardly on the helmet wherein said sound hole is configured to pass the audible sound through the ear hole, said bowl being exposed when said grommet is inserted into the ear hole wherein said bowl is configured to focus the audible sound at the ear hole in the helmet.

\* \* \* \* \*